United States Patent [19]
Hill et al.

[11] Patent Number: 6,095,147
[45] Date of Patent: Aug. 1, 2000

[54] METHOD FOR PHOTO-ALTERING A BIOLOGICAL SYSTEM TO IMPROVE BIOLOGICAL EFFECT

[75] Inventors: Richard A. Hill, Irvine; Daniel R. Doiron, Santa Ynez; David H. Crean, Santa Barbara, all of Calif.

[73] Assignee: The Regents of the University of California, Oakland, Calif.

[21] Appl. No.: 08/347,956

[22] Filed: Dec. 1, 1994

[51] Int. Cl.⁷ .................................................. A61B 19/00
[52] U.S. Cl. ............................................. 128/898; 604/4
[58] Field of Search ...................... 604/4–6, 20; 128/898; 514/410, 185, 2; 606/15–16; 424/9.61; 607/88–89

[56] References Cited

U.S. PATENT DOCUMENTS

| | | |
|---|---|---|
| 5,041,078 | 8/1991 | Matthews et al. ........................... 604/4 |
| 5,292,414 | 3/1994 | Sessler et al. ........................... 604/4 X |
| 5,432,171 | 7/1995 | Sessler et al. ........................... 604/4 X |
| 5,439,570 | 8/1995 | Sessler et al. ........................... 604/4 X |

OTHER PUBLICATIONS

Gomer et al. "Treatment of Intra Ocular Tumors With Hematoporphyrin Derivative Photo Radiation Therapy" Photochem Photobiol 39 (Suppl), 73S, Jul. 1984.

Garrett et al. "Photodynamic Therapy (PDT) of Exprimental Ocular Melanoma With Silicon Naphthalocyanine (SINc) in Rabbits," Investigative Ophthamology and Visual Science 35 (4). p. 2120, May 1994.

*Primary Examiner*—Mickey Yu
*Assistant Examiner*—Kelly O'Hara
*Attorney, Agent, or Firm*—Daniel L. Dawes

[57] ABSTRACT

Photodynamic therapy is a new adjunctive therapy for filtration surgery that does not use chemotherapy agents or radiation, but uses pharmacologically-active sensitizing compounds to produce a titratable, localized, transient, post operative avascular conjunctiva. A photosensitizing agent in a biological system is selectively activated by delivering the photosensitive agent to the biological system and laser activating only a spatially selected portion of the delivered photosensitive agent. The activated portion of the photosensitive agent reacts with the biological system to obtain a predetermined biological effect. As a result, an improved spatial disposition and effectuation of the biological effect by the photosensitive agent in the biological system is achieved.

20 Claims, 12 Drawing Sheets

METHOD FOR PHOTO-ALTERING A BIOLOGICAL SYSTEM TO IMPROVE BIOLOGICAL EFFECT

This invention was made with Government support under Contract No. 44514322443 awarded by the Department of Energy. The Government has certain rights in this invention.

BACKGROUND OF THE INVENTION

1. Field of the Invention

The invention relates to the field of ophthalmic medicine, and in particular to the augmentation of filtation surgery for the treatment of glaucoma by photodynamic therapy.

2. Description of the Prior Art

Glaucoma is a disease of the eye wherein the ocular pressure within the eye increases to a magnitude that optic nerve damage occurs and permanent blindness results. One of the prior art methods of treating glaucoma is to make an incision through the sclera of the eye, a trabecutomy, to provide a means by which the ocular fluid may escape and the pressure may be relieved. To prevent scar tissue from closing the incision and thereby rendering the overlying conjunctiva more permeable to the expressed intraocular liquid, an antimytotic agent is delivered to the conjunctiva to interfere with or block subsequent formation of fibrotic tissue.

The difficulty with this prior art technique has been that the delivery of the chemotherapeutic agent has been difficult to control both spatially and in terms of tissue uptake or dosage. The application of too high a dosage may result in destruction or serious damage to tissue well beyond simply interfering with the normal healing processes. Furthermore, even in cases where application and dosage of chemotherapeutic agents can be acceptably controlled, the long term effects of the use of such agents are only now becoming known and may be unacceptable. For example, it may be possible that by the use of such agents in a trabeculectomy may years later make the eye more susceptible to invasion by diseases than would normally be expected, or the eye pressure may go down too low causing a loss in vision.

Therefore, what is needed is some type of apparatus and method whereby diseases such as glaucoma may be surgically treated in a more controlled manner and with the minimization of possible side-effects.

BRIEF SUMMARY OF THE INVENTION

The invention is a method for selectively altering the histologic state of tissue in a biological system to in turn favorably alter wound healing and minimize fibrosis. The invention comprises the steps of delivering a photosensitive agent to the biological system and activating it with nonthermal light. Either the whole tissue area can be exposed to light and the localization effects of the photosensitive agent determines the treatment area, or the light can be delivered in a spatially selected manner thereby determining the treatment area. The activated photosensitive agent reacts with the biological system to obtain a desired biological effect. As a result, spatial disposition and effectuation of the biological effect by the photosensitive agent in the biological system is obtained.

The delivery of the photosensitive agent to the biological system comprises disposing the photosensitive agent only at a predetermined target tissue site or by a more systematic administration route in which the localizing properties of the photosensitizing agent targets the biological system. Selectively activating the photosensitive agent can comprise irradiating the photosensitive agent only in a predetermined target tissue location, or illuminating the agent over a broader area.

Irradiating the target tissue can comprise the steps of providing a radiation blocking mask and disposing the radiation blocking mask over the target tissue location. The mask has an aperture defined therein to expose only that portion of the target location which is desired to be irradiated. The mask including that portion of the mask in which the aperture is defined is irradiated so that only the selected portion is irradiated. Irradiating the target tissue location comprises selectively exposing the target tissue location to a predetermined level of light. For example, the exposure of the suture line can be avoided thereby decreasing the possibility of wound leakage and increasing the safety of the operation. In those applications where the localization of the photosensitive agent is sufficient use of the mask would not be needed.

The delivery of the photosensitive agent to the biological system must deliver the agent to a predetermined spatial location in a predetermined amount. Selectively activating the photosensitive agent comprises activating the agent with a predetermined light dosage in a selected portion of a target tissue location within the biological system. The light dosage and photosensitive agent concentration are interdependent to provide a net concentration of activated photosensitive agent in a predetermined spatial location of the target tissue location.

The method may further comprise photobleaching nonactivated and unreacted portions of the photosensitive agent to controllably stop the biological effect thereof.

The invention is also characterized as an improvement in a method for creating an ocular filter for the treatment of glaucoma comprising administering a photosensitive agent to a surgically created ocular bleb and photoactivating a spatially selected portion of the photosensitive agent introduced into the surgical site. The activated portion of the photosensitive agent is reacted with tissues comprising the bleb and adjacent thereto. As a result, controlled titration of the photosensitive reaction is achieved.

The invention is still further characterized as an apparatus for providing an improved titration of a photosensitive agent in a biological system comprising a light source and a first element for delivering a photosensitive agent to a target tissue location. A second element spatially and selectively photoactivates a portion of the photosensitive agent at the target tissue location. As a result, control of the biological effect of the photosensitive agent within the biological system at the tissue target location is achieved.

The apparatus further comprises at least one mask patch selectively disposed in the target tissue location to isolate an user selected portion from photoactivation.

The invention may be better visualized by now turning to the following drawings wherein like elements are referenced by like numerals.

The invention and its various embodiments may now be understood by turning to the following detailed description.

DETAILED DESCRIPTION OF THE PREFERRED EMBODIMENTS

Pharmacokinetics of the photosensitive agent or tin ethyl-etiopurpurin (SnET2) were studied after subconjunctival injections (0,25,50,75 ug; 11 rabbits). Noninvasive measurements were made at 0, 0.5, 1, 2, 3 and 4 hr postinjection using a HeCd based laser fluorescence diagnostic system (excitation-442 nm; detection-670 nm SnET2 fluorescence; tissue autofluorescense-570 nm). SnET2 uptake was determined by an elevated 670/570 nm ratio. Preoperative injections (0, 25, 50 and 75 ug; 8 rabbits) of SnET2 were given and posterior lip sclerectomies were performed after 3–4 hrs followed by post operative laser irradiation (665 nm; 100 mW/cm$^2$; 30 J/cm$^2$). Conjunctival fluorescence peaked at 3 hrs post injection with small, but detectable levels in the iris and optical axis. Self absorption of the fluorescence was present in the higher doses for the conjunctiva. Fluorescence ratios (T=3 hr) were as follows. The fluorescence ratios are shown below in Table 2. The tissue ratios were: conjunctiva/iris: 0 (control)=1.2; 25 ug=63+/−17; 50 ug=54+/−31; 75 ug=4+/−1.2. Conjunctiva/optical axis: 0 (control)=1.4; 25 ug=109+/−37; 50 ug=78+/−10; 75 ug=11+/−2.5. Post operatively, large transient areas of avascular conjunctiva were produced with limitation of avascular areas to filtering blebs at 4 weeks. Photodynamic therapy using SnET2 produced a titratable, localized, transient, post operative avascular conjunctiva. Photodynamic therapy may be a new adjunctive therapy for filtration surgery that does not use chemotherapy agents or radiation.

Figure 1:
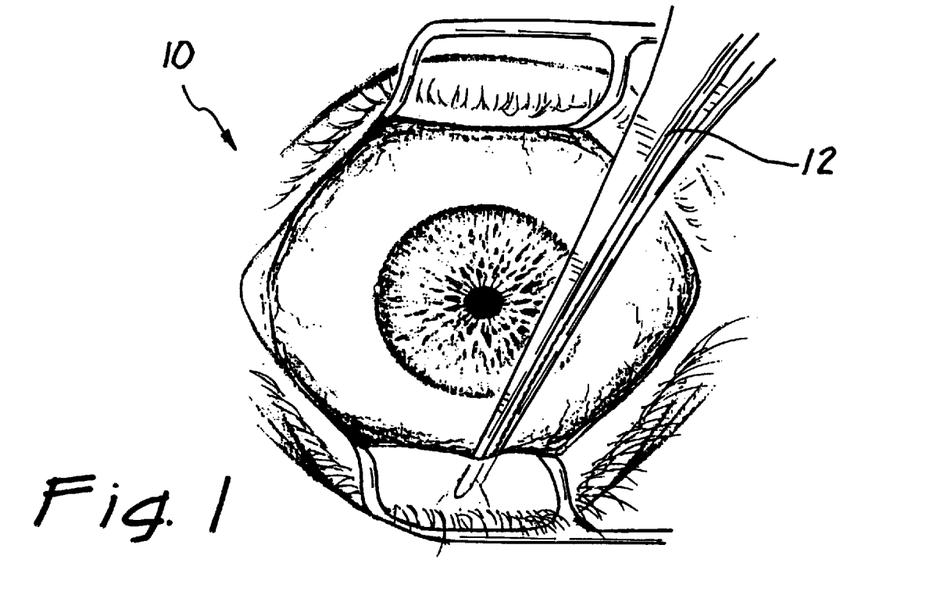
FIGS. 1–20 illustrate the steps in a trabeculectomy in which the apparatus and methodology of the invention is employed in one embodiment of the filtering surgery. Other filter surgeries could also be used in connection with the invention.
Figure 2:
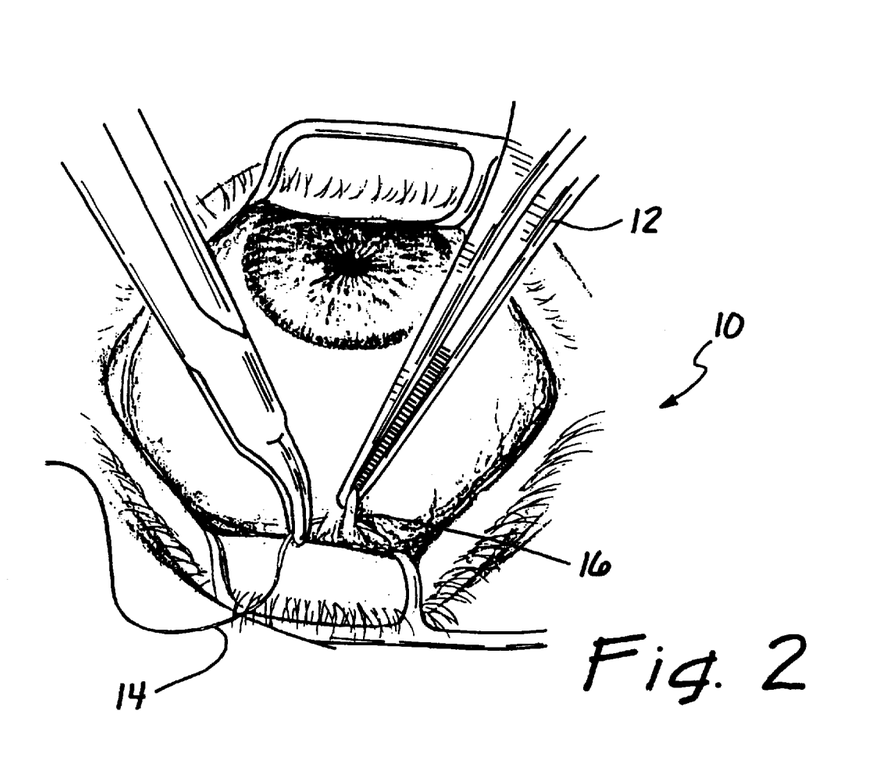
Figure 3:
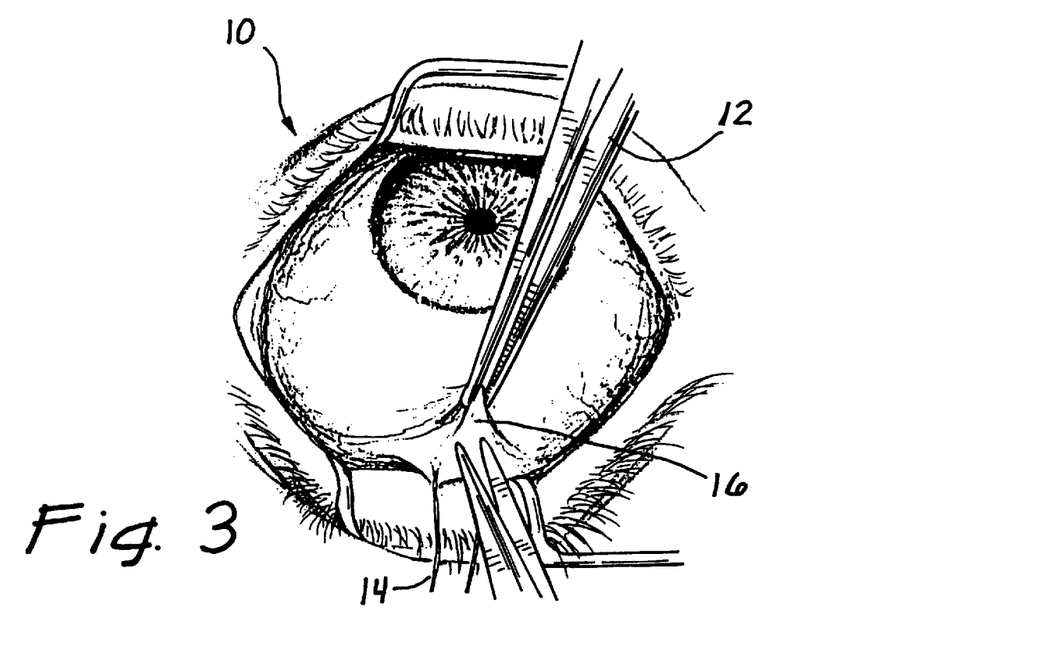
Figure 4:
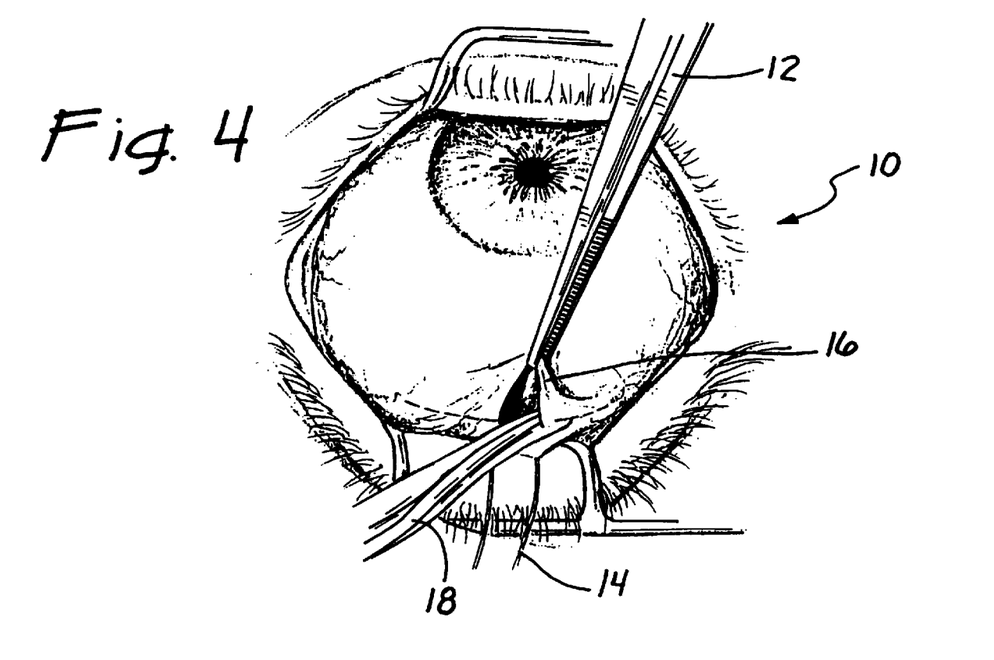
Figure 5:
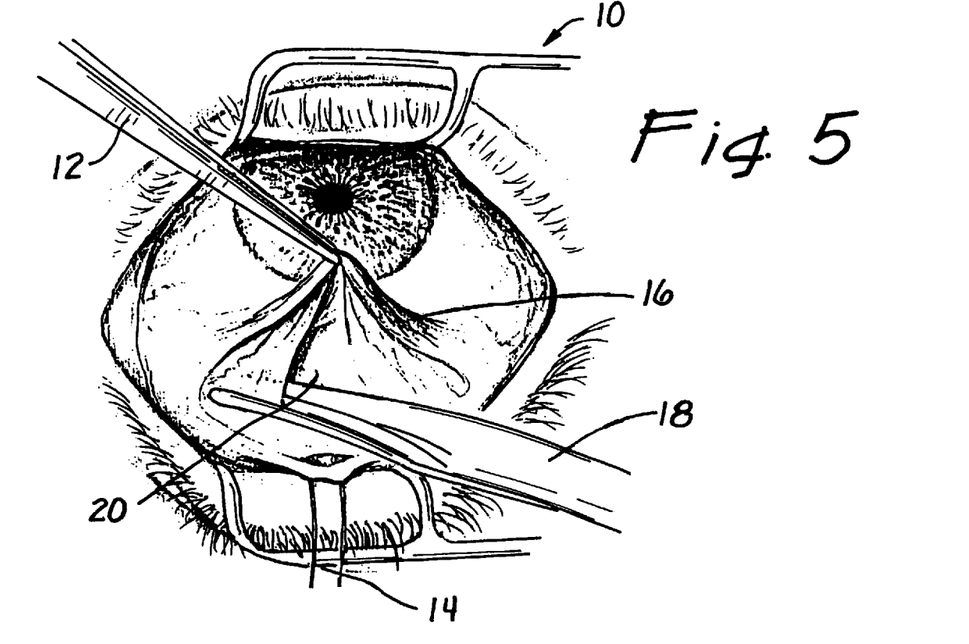

FIGS. 1–19 illustrate a conventional surgical technique, called a trabeculectomy, in which a filter or means is created within the human eye to lower intraocular pressure. The invention is not a surgical technique, but a method and apparatus which can be used in medical applications to make, for example, surgical techniques more effective. FIG. 1 illustrates a human eye 10 at the beginning of the procedure. The outer tissue layer of the eye, the conjunctiva, is grasped as high as possible in the cul-de-sac with forceps 12. As shown in FIG. 2, the tissue is pulled upwardly and a suture is placed under the muscle belly of the superior rectus muscle to create a bridal suture 14. With bridal suture 14 in place, as shown in FIG. 3, the conjunctiva 16 is grasped by forceps 12 as close as possible to bridal suture 14 and is cut immediately anterior to the superior rectus suture with scissors 18 as shown in FIG. 4. As shown in FIG. 5, the thicker, more opaque Tenon's capsule is grasped anterior to the conjunctiva incision and a hole defined therein or is buttonholed. The tips of scissor 18 are placed in the buttonhole and spread until the bare sclera 20 is visible. Tenon's capsule is lifted away from the globe of the eye and opened parallel to the previous conjunctiva incision of the same distance.

Figure 6:
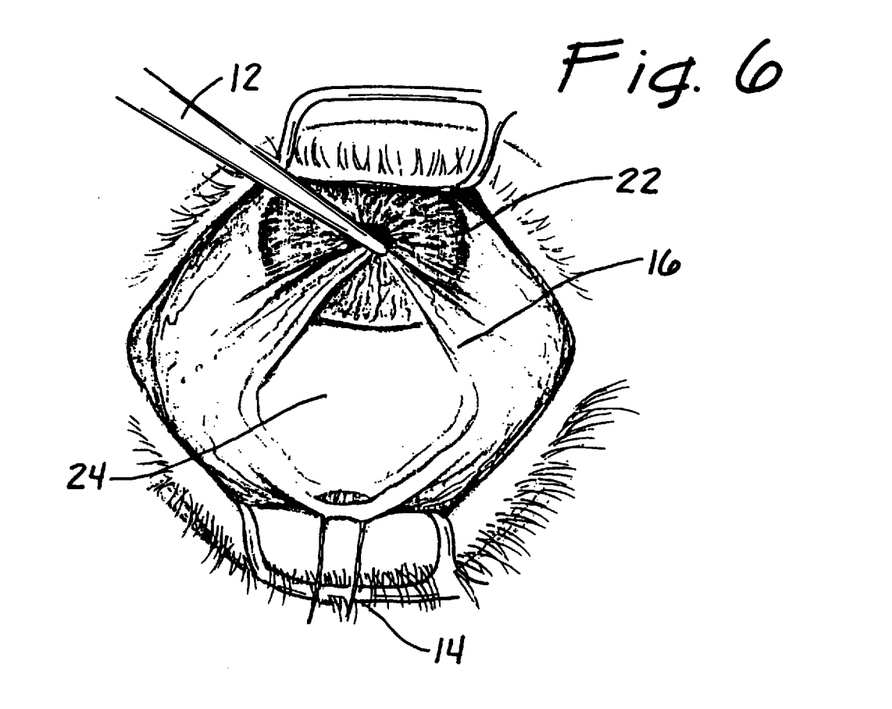
Figure 7:
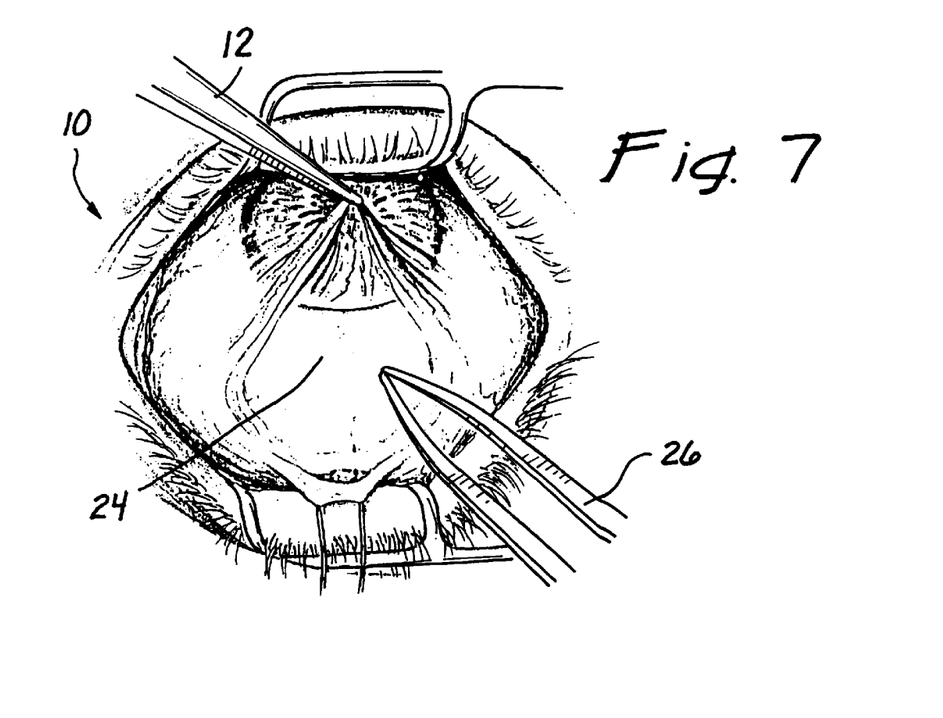

As the procedure continues in FIG. 6, a flap contained in Tenon's capsule and conjunctiva 16 is pulled anteriorly over cornea 22, exposing the episclera and sclera sulcus 24. As shown in FIG. 7 a bipolar cautery 26 is used to coagulate every vessel which is then bleeding so that all hemorrhage is stopped. Vessels which have stopped bleeding spontaneously are touched with an irrigator, and if they start bleeding again, are cauterized. The surface of the globe as well as the episclera and Tenon's flap are, therefore, rendered free of bleeding. At this point in the procedure the prior art treated the exposed episclera and conjunctiva with a chemotherapeutic agent, such as mitomyicin-C which would be absorbed and act to disrupt the overlying tissue such that fibrosis does not occur. This treatment step can be substituted in the invention by the administration of the photosensitive agent to the episclera and conjunctiva.

Next a flap, approximately 3–4 millimeters wide, parallel to the equator, and extending 3 millimeters posterior to the limbus on the median plane is outlined with cautery 26.

Figure 8:
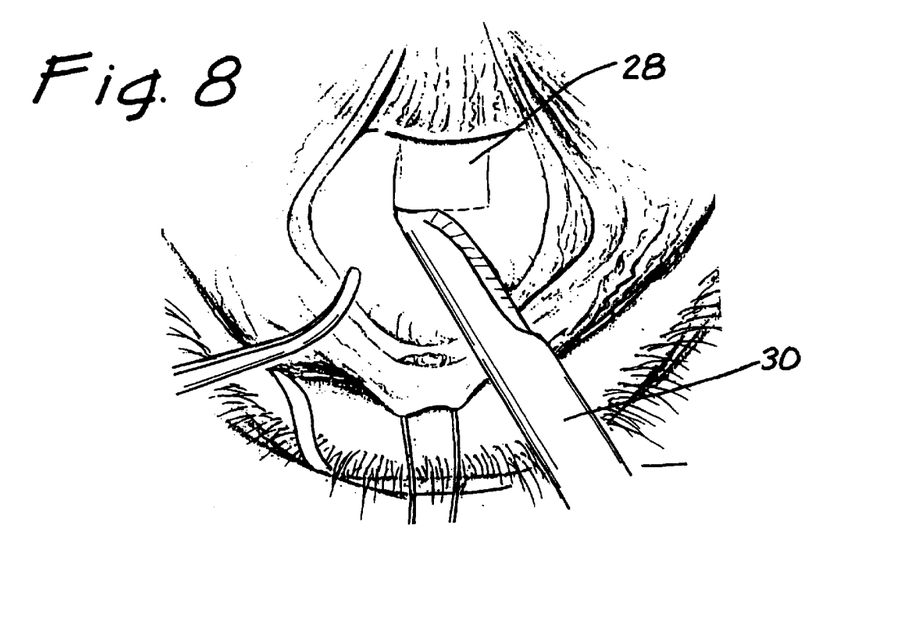
Figure 9:
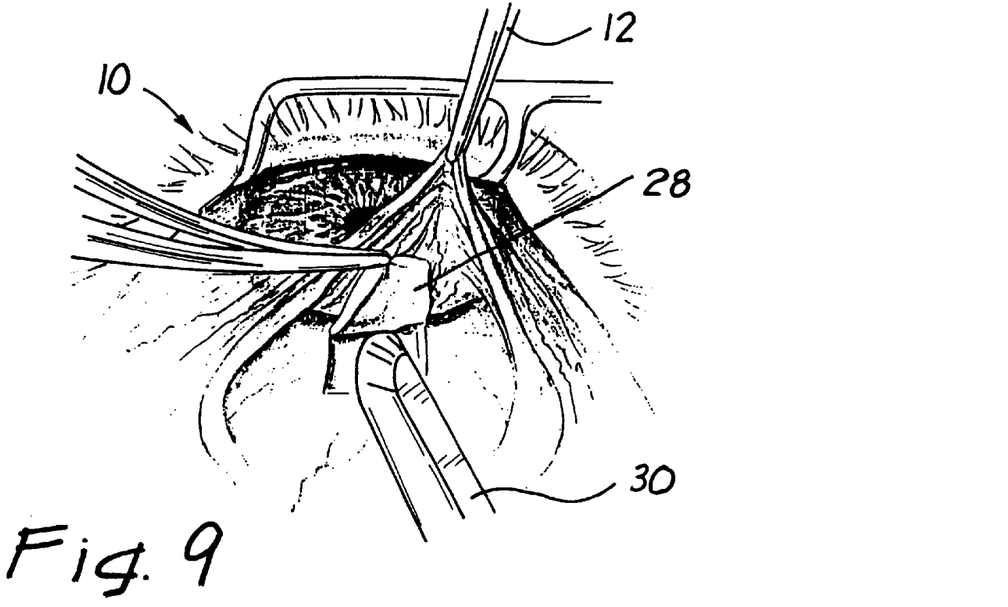
Figure 14:
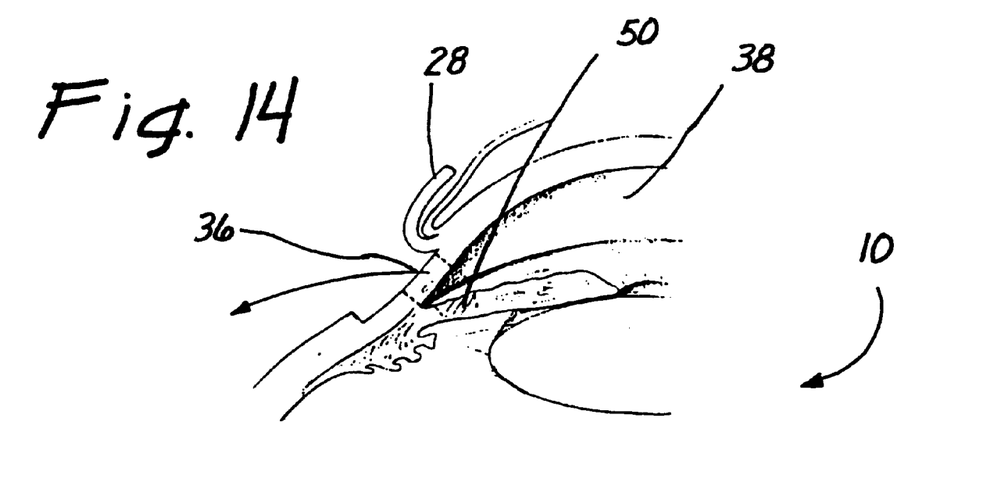

As shown in FIG. 8, a sclera flap 28 is defined with a scalpel 30 with a groove and with a variable thickness. As shown in FIG. 9, sclera flap 28 is the dissected completely across the posterior aspect is kept square as it is dissected anteriorly. The usual thickness of flap 28 is about one-third the total thickness of the sclera. The flap is dissected well into the clear cornea beyond the sclera sulcus. The flap extends well anterior to the iris roots so a block 50 of tissue anterior to the iris can be excised as is shown in FIG. 14.

Figure 10:
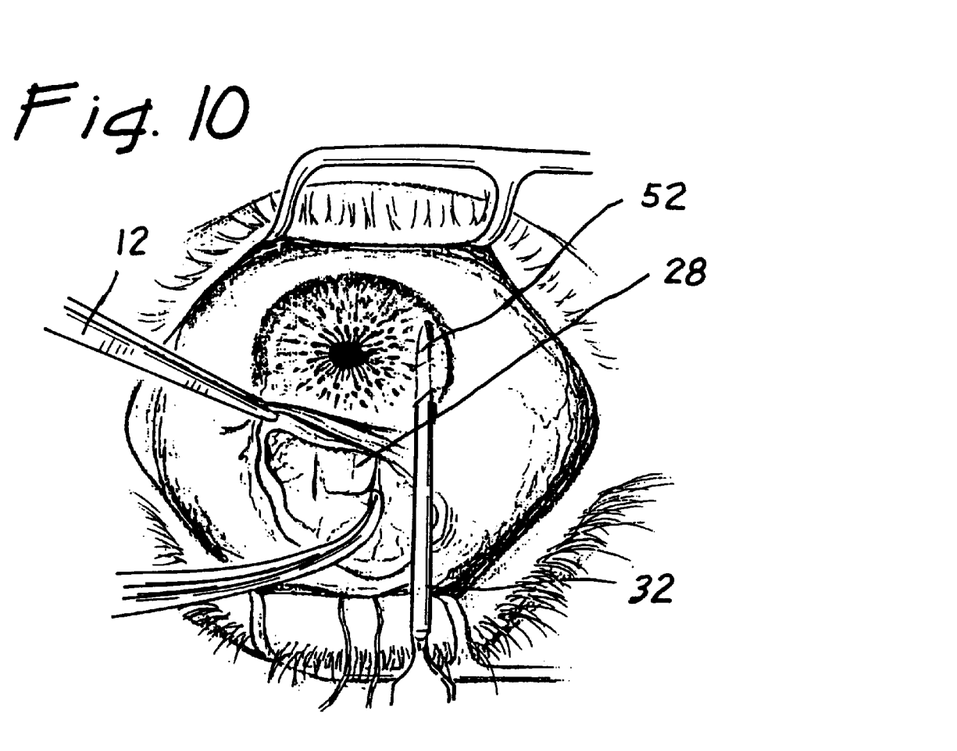
Figure 11:
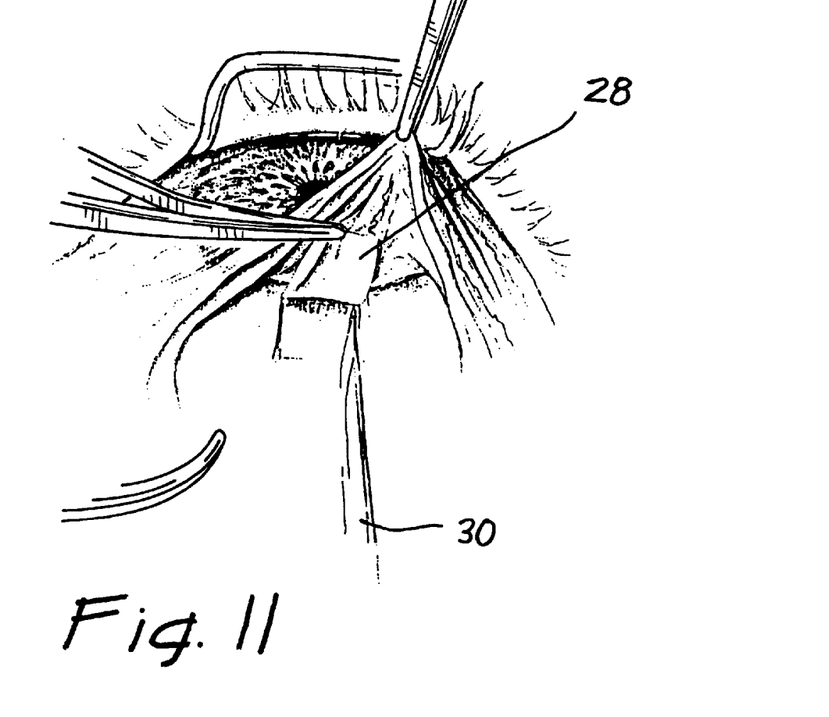
Figure 12:
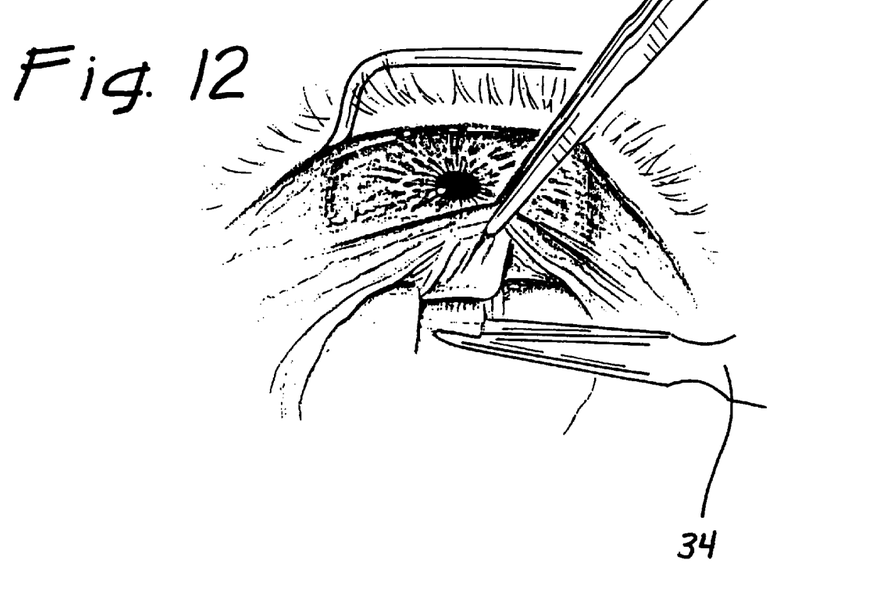

After a dissection of sclera flap 28 has been completed, a paracentesis track 52 is made using a knife 32. Penetration through the cornea is made to permit a track to be defined therein according to the surgeon's wishes, as shown in FIG. 10. With sclera flap 28 firmly fixated as shown in FIG. 11, an incision is made into the anterior chamber of the eye by knife 30. The radial groove is extended posteriorly until it reaches opaque, white sclera, just posterior to the position of Schlemm's canal. Scissors 34 are inserted into an area of the clear cornea as shown in FIG. 12 and the posterior edge of an internal block of sclera is incised with scissors 34 as shown in FIG. 12.

Figure 13:
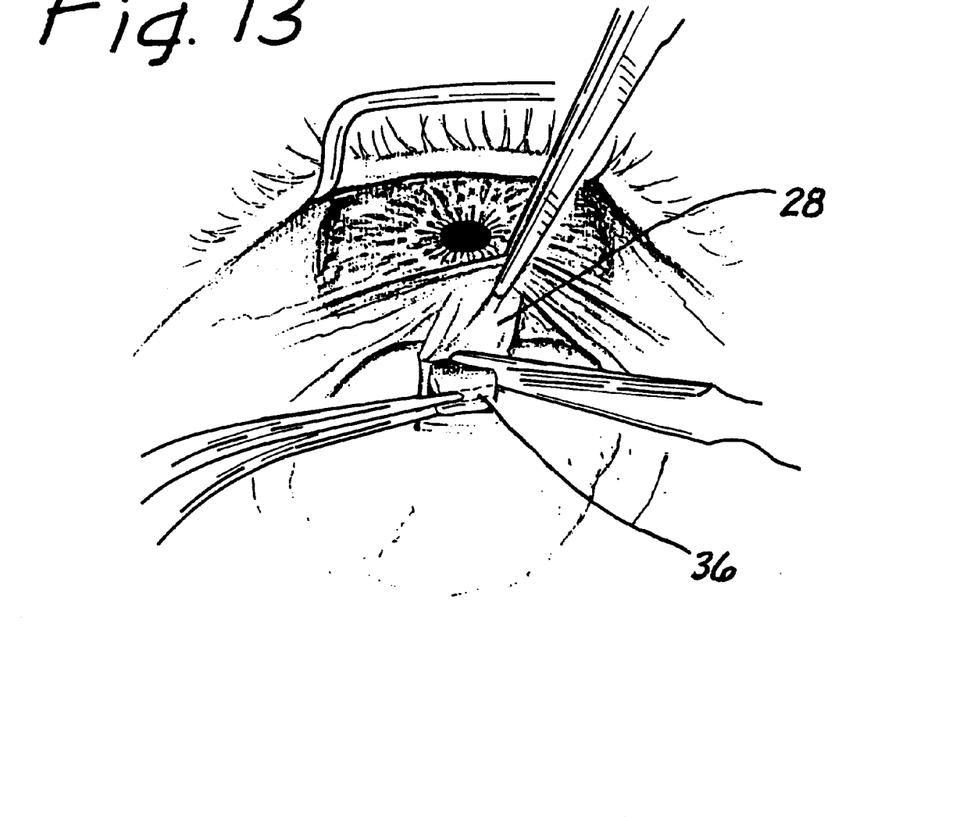

Grasping an internal block 36 at its posterior edge, block 36 is pulled posteriorly as shown in FIG. 13. Block 36 is then amputated as far interiorly and squarely as possible with scissors. FIG. 14 shows a simplified cross-sectional view of the amputation of block 36 thereby opening a passageway into anterior chamber 38 of eye 10.

Figure 15:
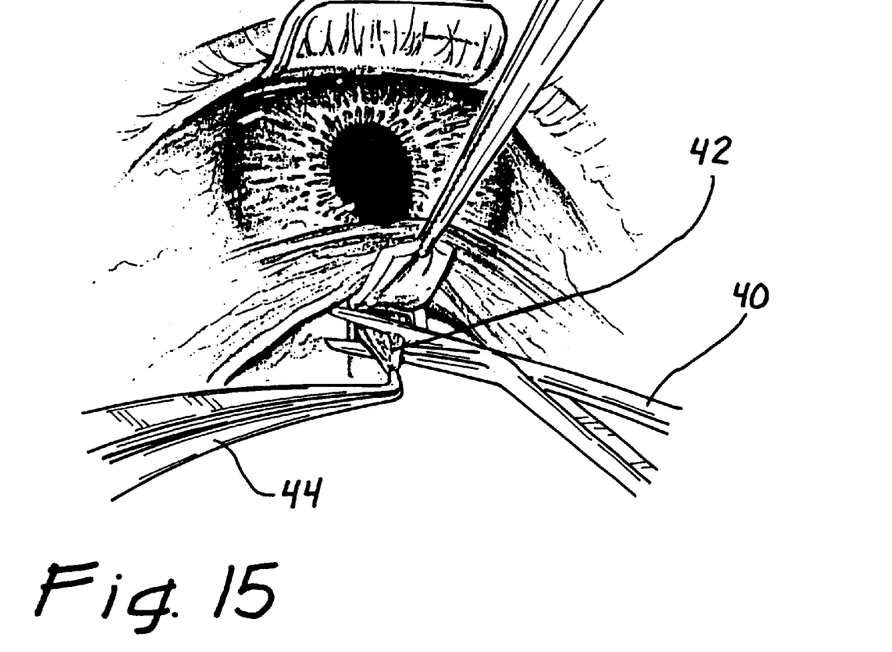
Figure 16:
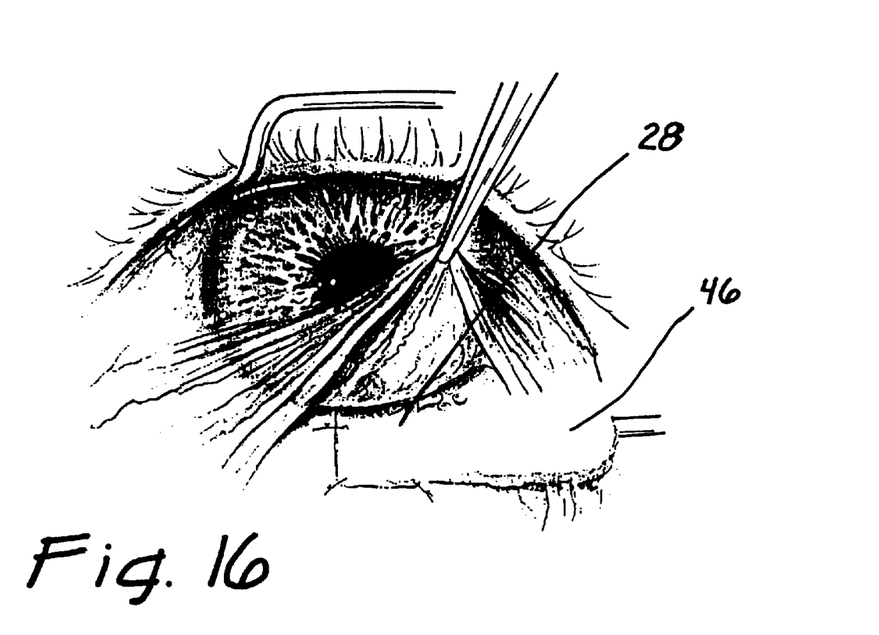
Figure 18:
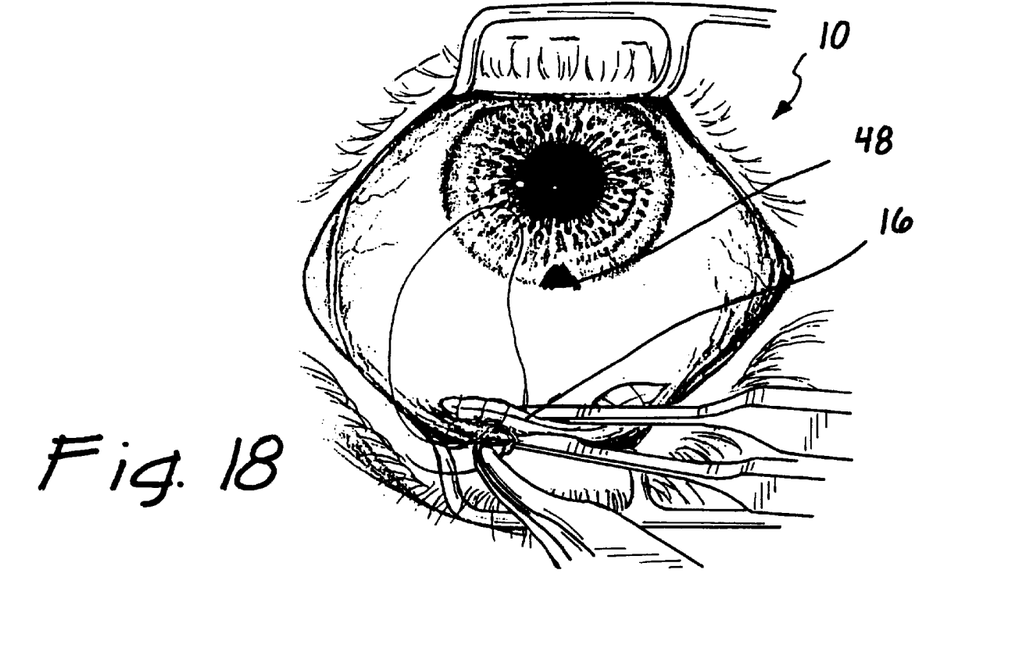

A large iridectomy is then performed as shown in FIG. 15 using iris scissors 40, making sure that the iridectomy is greater than size of internal block sclera 36 just removed. A portion 42 of the iris is then pulled through the opening left by block 36 by means of tweezers 44 and removed by scissors 40 to define an opening 48 as shown in FIG. 18. Sclera flap 28 is then closed as shown in FIG. 16 by suturing. The anterior chamber 38 of the eye is filled with balanced salt solution through the paracentesis track 52 created in FIG. 10 and the amount of leakage through sclera flap 28 determined, for example, by means of test absorption through a cellulose sponge 46. If leakage is judged excessive, additional sutures are placed. If leakage is insufficient, a suture may be removed or a cautery lightly placed at the edge of sclera flap 28 in order to produce separation of the edges and increase the leakage.

Figure 17:
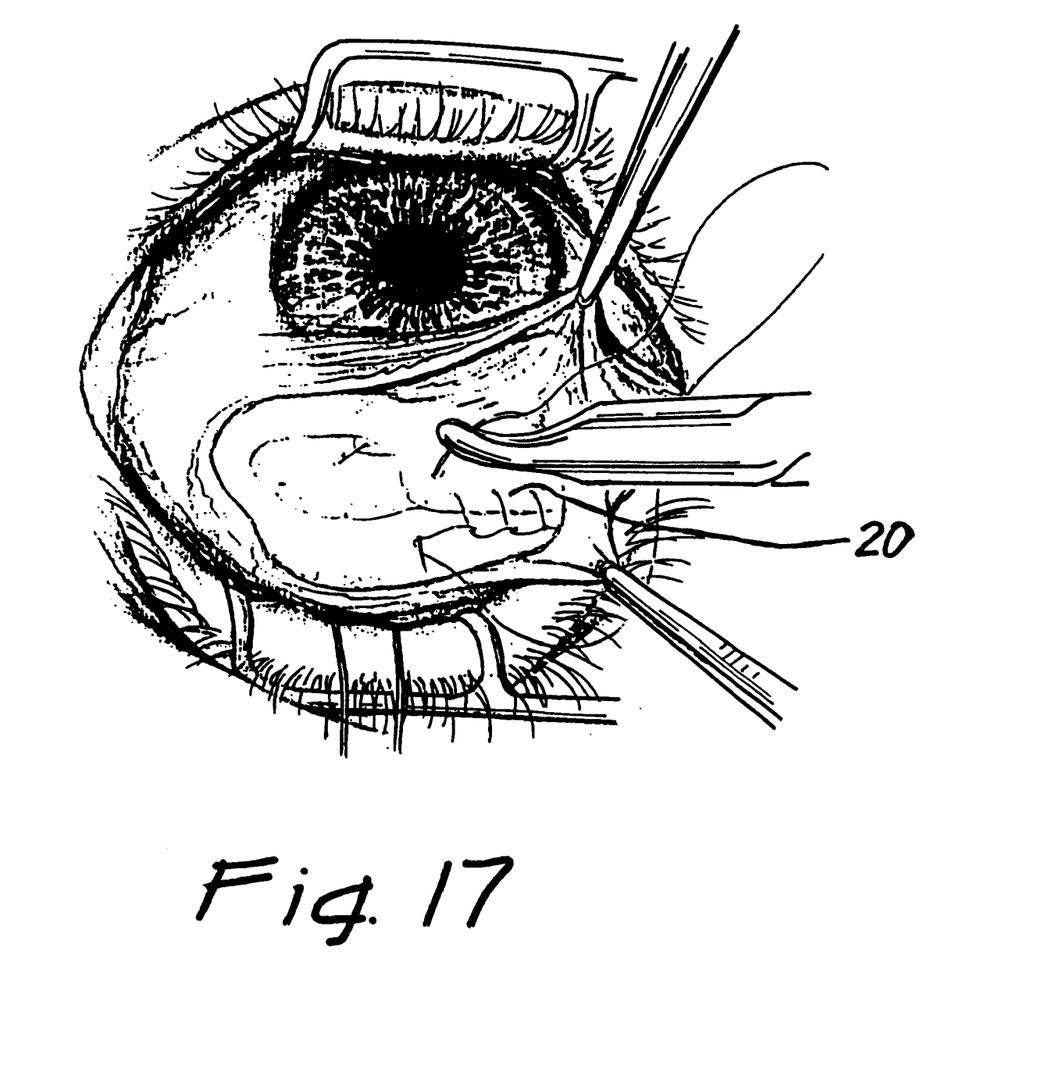

Tenon's capsule 20 is then closed as shown in FIG. 17 with sutures, followed by closure of the conjunctiva 16 by suturing as shown in FIG. 18. The opening 48 defined in iris created by removal of tissue section 50 shown in cross sectional view of FIG. 14 is clearly depicted in FIG. 18.

Figure 19:
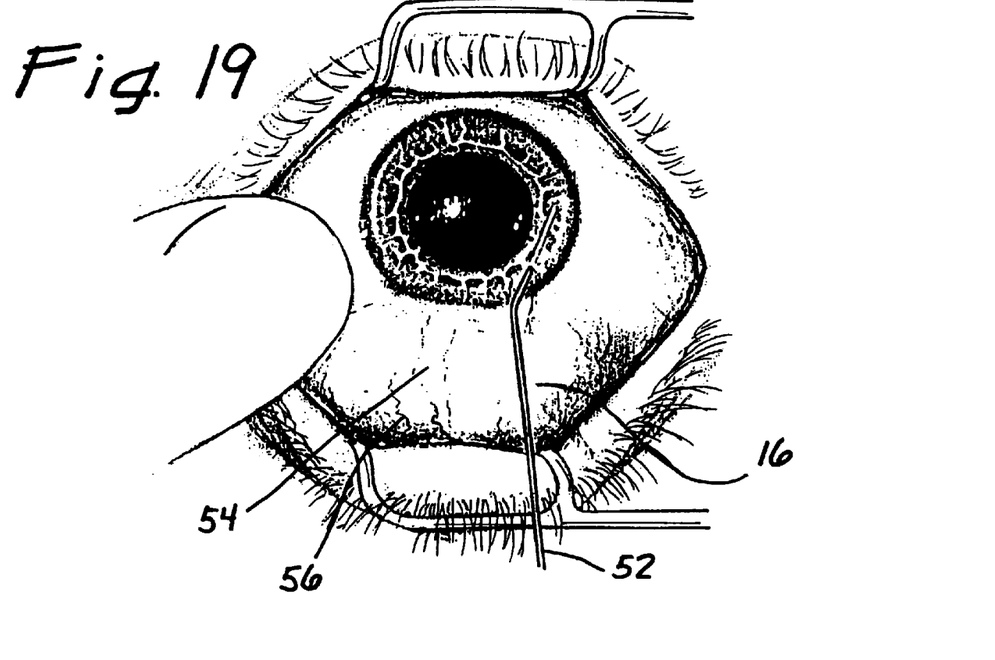

By the stage of the procedure shown in FIG. 19, anterior chamber 38 of eye 10 has again filled with balanced salt solution through the paracentesis track 52. As anterior chamber 38 shown in FIG. 14 is filled with solution, a bleb 54 develops in the lower portion of the eye. At this point, vessels 56 in the vicinity of bleb 54 must be treated so that fiberblasts do not proliferate into the tissues overlying the leaking sclera flap 28. Otherwise fibrotic tissue would be formed and ocular fluid leakage may cease. In fact, if no further treatment were undertaken at least 50% of the cases with previous surgery would scar down and all leakage would stop.

Figure 20:
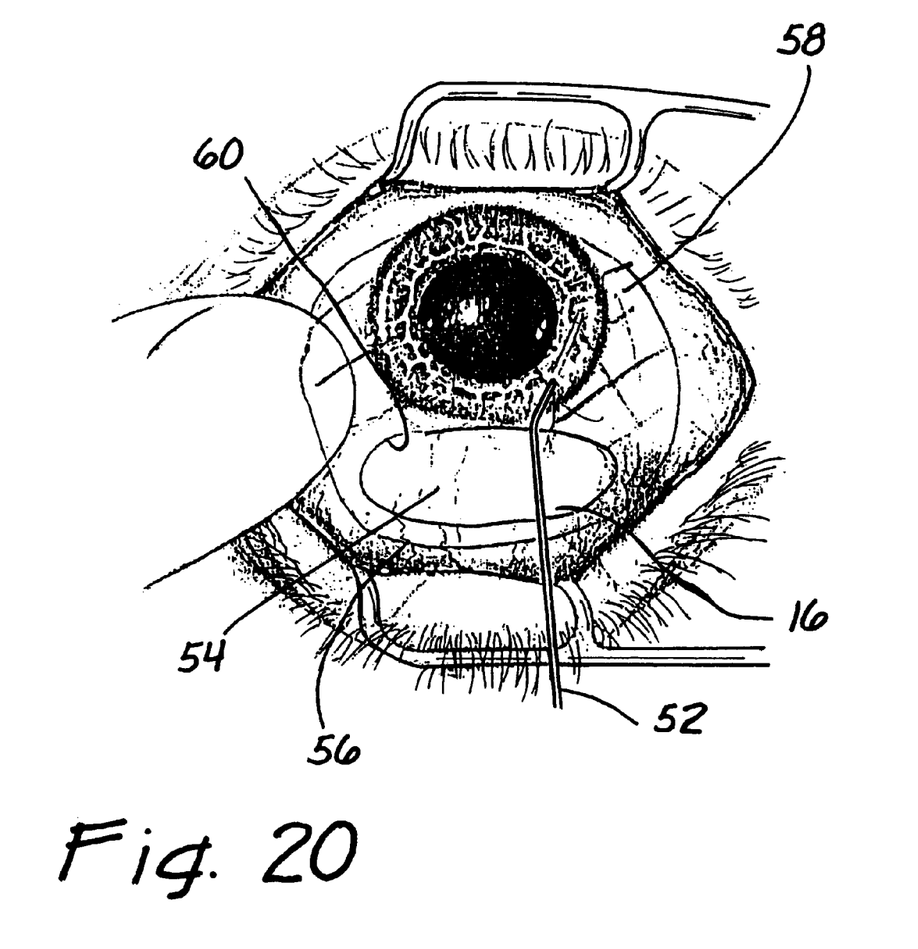

According to the invention, conjunctiva 16 in the area of bleb 54 and the underlying tissues are treated instead at this point with a photosensitizing agent. FIG. 20 illustrates the condition of the eye as in FIG. 19 in which an opaque mask 58 has been disposed in contact over the eye and in which an aperture 60 is defined, leaving a selected portion of the underlying conjunctiva 16 exposed. Aperture 60 typically exposes the portion of bleb 54 through which fluid leakage is intended to occur. The photosensitive agent is delivered, such as by injection, into bleb 54 and surrounding tissues. This delivery may be initiated at the stage shown in FIG. 20 or may be injected several hours earlier depending on the agent and effect desired by the surgeon.

After the photosensitizing agent has achieved proper spatial distribution, the eye is exposed to a predetermined intensity of light for a predetermined time in order to activate the photosensitizing agent. After the photosensitizing agent has been exposed with a light dose or intensity beyond a predetermined threshold, the agent is activated and forms oxidizing compounds which quickly react with the immediately adjacent tissue to alter or change their histological state. This includes forming a thrombosis in each of blood vessels 56 in the exposed area and thereby preventing fibrosis. As a result the filtering properties of surgical bleb 56 are permanently retained.

In the illustrated embodiment the light exposure occurs at the stage of the operation illustrated by FIG. 20. However, it is also contemplated that light exposure could be provided during the entire operation through the surgeon's microscope if the photosensitive agent were properly delivered to the target tissues prior to exposure, and if the spectral and power parameter of the illumination match that required by the specific photosensitive agent used.

If a buttonhole accidentally occurs in conjunctiva 16, an opaque patch 59 may be disposed into contact with conjunctiva 16 over the buttonhole, the surrounding tissue of which is then shielded from photoactivation of the photosensitive agent. Later the buttonhole will heal and close without interference from any activated agent thereby avoiding the complications which might otherwise follow from the existence of such small buttonholes in the face of widespread application of a chemotherapy agent as occurred in the prior art.

It must be understood that details of the method and the apparatus by which both the photosensitizing agent and light are delivered can be varied in many different ways without departing from the scope and spirit of the invention. For example, the route of administration of the photosensitizing agent can be through any number of pathways. In the past, the most common pathway for photosensitive agents has been by intravenous injection following a specific uptake in a target tissue of unknown histological type, usually a cancer tissue. In the preferred embodiment of FIG. 20, local injection at the tissue target location is preferred, but systematic application through intravenous injection, topical applications, suppository, time-released, oral administration or iontophoresis of a photosensitizing agent could be used as well if appropriate. Local injection of a gelatinous carrier in which the photosensitizing agent is bound or included may be utilized as a further means of restricting the spatial disposition of the agent. Injection may be intravascular, intraperitoneal, intramuscular, intrathecal or subcutaneous depending on the target tissue location. Also topical application of the photosensitive agent to the bleb area might be used. Topical application may be by creams, fluids by instillation or retention, or by coated or impregnated patches. Where administration is by suppository it may be rectal or vaginal. Where by extend time release, it may be by implantable device, vascular stent, tablet or capsule. Iontophoresis is a method of driving a charge-carrying agent into tissue using electrical fields and is well suited in this application to spatially selectively deliver the agent.

Similarly, the delivery of light to the tissue target location defined by aperture 60 can also be provided by many different vehicles. In general, illumination can occur through noncontact illumination, contact illumination, or interstitial illumination. Noncontact illumination is the shining of light upon the all or most of tissue target location defined by an aperture 60 without having any part of the light source itself touching the treatment area. For example, a light source can be focused or otherwise directed onto the tissue target location from a separate optical system, or through the physician's microscope used in the surgical arena.

Contact illumination contemplates an illumination source which is actually placed in contact with the treatment area, such as would be the case when using a fiber optic contact probe. Contact illumination allows more localized delivery of the light and may be used, for example, with or without mask 58, which in the preferred embodiment is primarily intended to be used with noncontact illumination.

Light could also be delivered to the target area using small fiberoptic probes that are directly inserted into the tissue as interstitial illumination. In this manner, the delivery of light at predetermined depths within the target tissue may be increased and more closely controlled than by surface contact or noncontact illumination methods.

In the illustrated embodiment red light is used because it matches one of the absorption peaks of SnET2. Other wavelengths would be used with different agents as long as they match the absorption spectrum of the photosensitive agent. In addition other absorption peaks for SnET2 might be used in or outside the visible spectrum, since accurate aiming of the light beam is not critical when the location of the exposure is controlled by mask 58. Shorter wavelengths of light might also be used to avoid deeper penetration and scattering in the tissue. For example, blue light penetrates the tissue substantially less than red light and thus might be preferably used in applications where depth of reaction needed to be better controlled.

Any number of photosensitive agents may be employed in the methodology for the photodynamic therapy. For example, in the preferred embodiment, tin ethyl-etiopurpurin (SnET2) is used as a photosensitizing agent. However, any photosensitizing agent which is capable of removing the vascularity of the target tissue and keeping the fibrosis process from occurring, which process destroys the filtering properties of bleb 54, could be substituted. Photosensitizing agents which are deemed as possible or actual substitutes for SnET2 are set forth below in Table 1.

TABLE 1

PHARMACOLOGICALLY-ACTIVE SENSITIZING COMPOUND
CLASSES FOR PHOTODYNAMIC THERAPY

Pyrrole-derived macrocyclic compounds
Naturally-occurring or synthetic porphyrins and derivatives thereof
Naturally-occurring or synthetic chlorins and derivatives thereof
Naturally-occurring or synthetic bacteriochlorins and derivatives thereof
Synthetic isobacteriochlorins and derivatives thereof
Phthalocynanines and derivatives thereof
Naphthalocynanines and derivatives thereof
Porphycenes and derivatives thereof
Sapphyrins and derivatives thereof

TABLE 1-continued

PHARMACOLOGICALLY-ACTIVE SENSITIZING COMPOUND CLASSES FOR PHOTODYNAMIC THERAPY

Texaphyrins and derivatives thereof
Anthrapyrazoles and derivatives thereof
Phenoxazine dyes and derivatives thereof
Phenothiazine and derivatives thereof
Chalooganapyrylium dyes and derivatives thereof
Triarylmethanes and derivatives thereof
5-Aminolevulinic acid
Inhibitors of protoporphyrin oxidase Still further, although the preferred embodiment has described a single application or administration of the photosensitizing agent and a single photoactivation at the end of the surgical procedure, it is to be expressly understood that multiple applications or administrations could be employed or a vehicle which provided a sustained released administration also equivalently substituted. Activation could be implemented with one exposure or a cycle of exposures.

The preferred embodiment of the invention has been described in the context of a trabeculectomy for the treatment glaucoma, but the specific illumination of a delivered photosensitizing agent disposed in a confined spatial disposition as taught here can be used in many other applications for diagnosis and treatment of biological or medical conditions. Specifically, the apparatus and methodology in the invention may be used in the diagnosis and treatment of diseases or other conditions which generate lesions or in the elective diagnosis and alteration of normal conditions to obtain a desired effect. More specifically, the method and apparatus of the invention is expected to be used in treatment of tumors or neoplasms, infections, hyperpoliferating cells or tissues, hyperplasia, dysplasia, vascular or other types of malformations and inflammation.

In terms of biological mechanics, the photodynamic therapy of the invention can be used in tissue or cell modification, removal, stasis or destruction without the necessity of removal as occurs in the illustrated embodiment where the capillaries in the filter are destroyed and permanently removed.

The dosage of the photosynthesizing agent and the length and intensity of illumination will vary depending upon the type of application and the photosensitizing agent selected. It is now just becoming understood that there are two competing processes which are taking place when a photosynthesizing agent is irradiated. The first is the photoactivation of the process. The photoactivation rate differs with each agent. Simultaneously, or at least concurrently therewith, photobleaching occurs where the activation or irradiation destroys the photosynthesizing agent itself. The rate of photobleaching is generally different than the rate of photoactivation, and it is thought to increase more quickly with intensity than does photoactivation.

Therefore, it is included within the scope of the invention that the irradiation in combination with a predetermined delivered amount of photosensitive agent could occur so that in the first stages of exposure, the delivered photosensitizing agent is activated and combines with the target tissue to achieve the degree of desired tissue or cell destruction. Thereafter, the photobleaching rate overtakes the photoactivation rate, and the activated photosensitizing agent, which has not yet combined with tissue, is bleached or rendered inactive by continued irradiation. This then brings the biological effect of the photosensitizing agent to a stop so that further shielding from light in the postoperative period becomes unnecessary and the opportunity for uncontrolled continued biological action will not occur.

For example as shown in Table 2 below, SnET2 in the microgram amounts shown in the leftmost column was injected into the conjunctiva of rabbits. Noninvasive fluorescent measurements, using a HeCd laser, was made of the SnET2 to determine its uptake and distribution. Exposure of SnET2 with a HeCd laser, excites the tissue at 442 nanometers and detects 670 nanometer florescence for SnET2 and 570 nanometer for tissue autofluorescence. The higher the ratio (670 nm/570 nm), the higher the uptake. Measurements in the conjunctiva compared to the iris and of the conjunctiva as compared to the axis of the eye, namely the pupil, were compared three hours after injection. Table 2 shows the actual fluorescence measurement (the ratio of 670 nm to 570 nm) where the increasing injected dose shows an increased fluorescence signal in all cases except for the 75 ug conjunctiva case. In this case the self-absorption of the 670 nm fluorescence by the SnET2 at such a high local concentration causes the intensity to actually decrease. Also note that in the 50 ug case the fluorescence also does not linearly increase from the 25 ug case. This is also due to self-absorption. Note that for the iris and axis readings the signal does continue to increase with increasing injected dose due to the greater leakage into these areas of the eye with the higher injected doses. This is a negative, unwanted effect and is why the ratios of the conjuntiva/iris and conjuntiva/axis ratios decrease in Table 3. This data supports the conclusion that lower drug doses should be given. Table 3 gives the ratio comparisons for the different ocular tissues. The decreased tissue ratios at the higher photosensitizer injection doses indicate lower specificity due to greater leakage from the injection site.

TABLE 2

Fluorescence Ratios (670 nm/570 nm) of Ocular Tissues After SnET2 Subconjunctival Injection

| SnET2 Concentration ($\mu$g) | No. Animals | Time (hr's) | Conjunctiva Fluorescence Ratio (670 nm/570 nm) | Iris Fluorescence Ratio (670 nm/570 nm) | Axis Fluorescence Ratio (670 nm/570 nm) |
|---|---|---|---|---|---|
| 0.0 (Control) | 1 | — | 0.24 | 0.20 | 0.17 |
| 25 | 3 | 3 | 28.27 +/− 10.90 | 0.44 +/− 0.08 | 0.26 +/− 0.03 |
| 50 | 3 | 3 | 31.70 +/− 8.60 | 0.65 +/− 0.21 | 0.37 +/− 0.05 |
| 75 | 5 | 3 | 15.14 +/− 13.60 | 4.72 +/− 4.94 | 1.30 +/− 0.90 |

TABLE 3

Ratios of Tissue Fluorescence Values Demonstrating SnET2 Selectivity

| SnET2 Concentration (μg) | No. Animals | Time (hr's) | Ratio of Fluorescence (Conjuctiva/Iris) | Ratio of Fluorescence (Conjuctiva/Axis) |
|---|---|---|---|---|
| 0.0 (Control) | 1 | — | 1.2 | 1.4 |
| 25 | 3 | 3 | 63 +/− 17.0 | 109 +/− 37.0 |
| 50 | 3 | 3 | 54 +/− 31.0 | 78 +/− 10.0 |
| 75 | 5 | 3 | 4 +/− 1.2 | 11 +/− 2.5 |

Table 2 illustrates that the injected SnET2 is preferentially taken up and preferentially remains in the area of the injection, namely the conjunctiva. In the Table decreasing numbers at higher concentration rates are indicative of actual decreased uptake in the nontargeted tissues (iris layer), in addition to self-absorption of the fluorescence by the SnET2 compound itself as the concentration increases. It is presently expected that injections of about 25 micrograms and less are likely to provide the best selective biological results.

Some of the animals of the group shown in Table 2 and 3 were treated with 665 nanometers laser light at 100 milliwatt per square centimeter (30 Joules per square centimeter) exposure with 8 millimeter diameter spot three to four hours after the injection of the SnET2 following filtering surgery in the eye.

Figure 21:
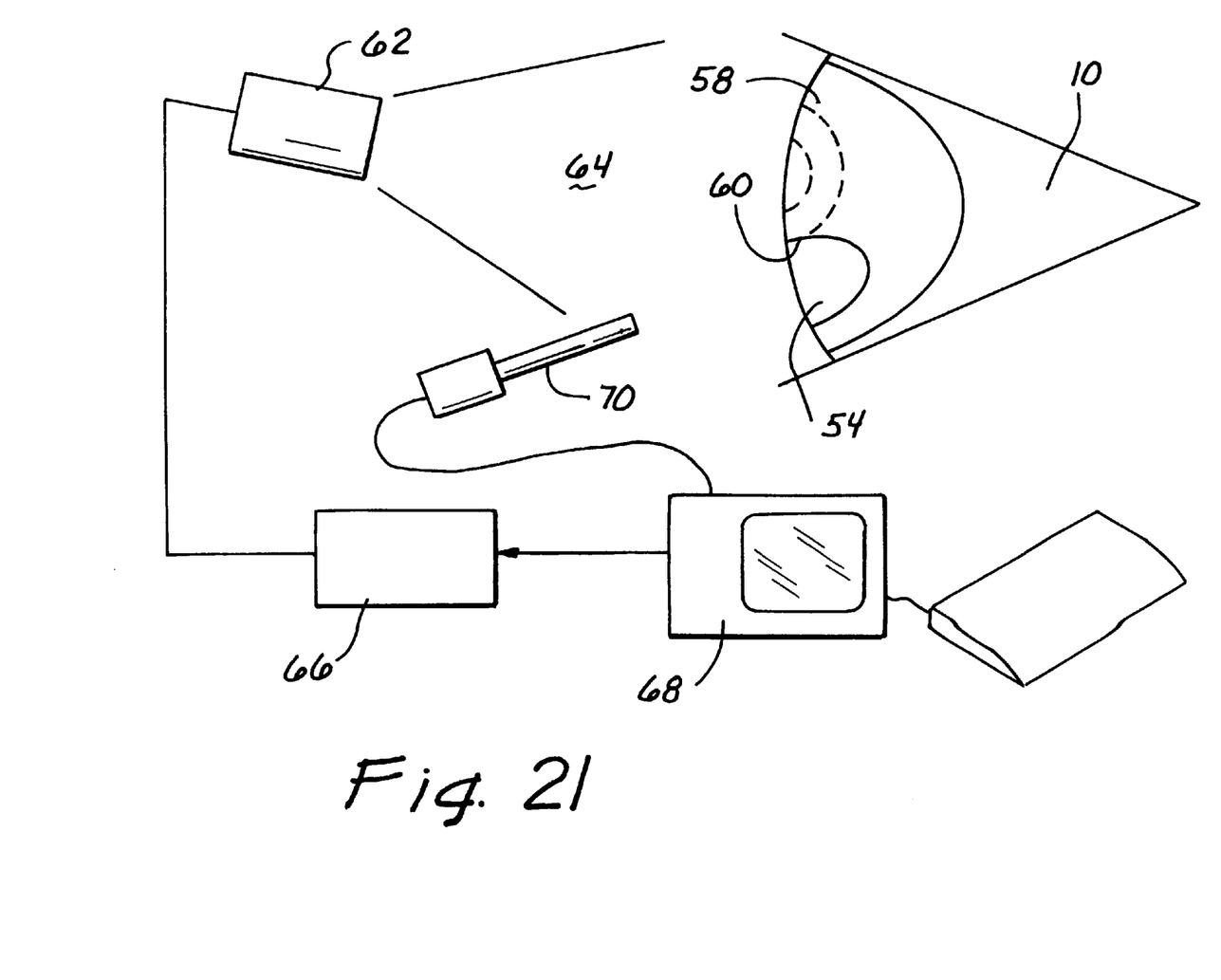
FIG. 21 is a block diagram of an apparatus of one embodiment of the invention.

FIG. 21 is a diagrammatic illustration of a system in which the preferred embodiment is realized. Light is generated by a diode laser light source 62, which is coupled to an optic fiber, the output of which is directed onto the mask 58, which through aperture 60, only exposes a selected portion of bleb 54. Light source 62 is powered by and controlled by a controller 66, which controls the intensity and timing of the light exposure. Exposure may not only be multiple, but may also be continuous or pulsed according to user selected input through computer terminal 68. If desired, the output of a fiberoptic detector probe 70 can be provided to computer terminal 68 to measure both the photosensitizer florescence and excitation florescence or fluence (irradiation×time) at the tissue surface to assist in determining the optimum treatment parameters.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result.

In addition to the equivalents of the claimed elements, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A photodynamic surgical method comprising:
   delivering a photosensitive agent to biological tissue in a spatially controlled manner, said photosensitive agent characterized by production of a predetermined biological effect in said tissue when said photosensitive agent is activated and reacted with said tissue;
   activating a spatially selected portion of said photosensitive agent with electromagnetic radiation by spatially controlled exposure to said electromagnetic radiation of said biological tissue having said photosensitive agent disposed therein; and
   reacting said activated photosensitive agent in said biological tissue to obtain said predetermined biological effect.

2. The method of claim 1 where delivering said photosensitive agent to said biological tissue comprises disposing said photosensitive agent only at a predetermined target tissue site within said biological tissue.

3. The method of claim 2 where disposing said photosensitive agent comprises injecting said photosensitive agent at said target tissue location.

4. The method of claim 2 where disposing said photosensitive agent comprises topically administering said photosensitive agent at said target tissue location.

5. The method of claim 2 where disposing said photosensitive agent comprises systematically administering said photosensitive agent at said target tissue location.

6. The method of claim 2 where disposing said photosensitive agent comprises orally administering said photosensitive agent at said target tissue location.

7. The method of claim 2 where disposing said photosensitive agent comprises administering said photosensitive agent at said target tissue location by iontophoresis.

8. The method of claim 2 where disposing said photosensitive agent comprises in combination at least two of steps selected from the group of steps of injecting, topically administering, orally administering, systematically administering and iontophorerically administering said photosensitive agent at said target tissue location.

9. The method of claim 1 wherein activating a spatially selected portion of said photosensitive agent with electromagnetic radiation comprises irradiating said photosensitive agent only in a predetermined target tissue location.

10. The method of claim 9 where irradiating said photosensitive agent comprises:

providing a radiation blocking mask;

disposing said radiation blocking mask over said target tissue location, said mask having an aperture defined therein to expose only that portion of said target location which is desired to be irradiated; and irradiating said mask including that portion of said mask in which said aperture is defined so that only said selected portion is irradiated.

11. The method of claim 9 where irradiating said target tissue location comprises selectively exposing said target tissue location to a predetermined level of light.

12. The method of claim 10 where irradiating said target tissue location comprises selectively disposing said target tissue location to a predetermined level of light.

13. The method of claim 1 further comprising controlling said activating of a spatially selected portion of said photosensitive agent with electromagnetic radiation by real time feed-back based on comparative measurements of fluorescence and fluence.

14. The method of claim 1 where in the step of delivering of said photosensitive agent to said biological tissue, said agent is delivered to a predetermined spatial location in a predetermined amount; and where the step of activating a spatially selected portion of said photosensitive agent with electromagnetic radiation comprises activating said agent with a predetermined light dosage in a selected portion of a target tissue location within said biological tissue, said light dosage and photosensitive agent concentration being interdependent to provide a net concentration of activated photosensitive agent in a predetermined spatial location of said target tissue location.

15. The method of claim 14 where activating a spatially selected portion of said photosensitive agent with electromagnetic radiation comprises providing a contact mask on said target tissue location to block said light at a first portion of said target tissue location and permit irradiation at a second portion of said target tissue location.

16. The method of claim 14 where selectively activating said photosensitive agent comprises providing a selective disposition of said photosensitive agent only at selected portion of said target tissue location and irradiating all of said target tissue location.

17. The method of claim 1 further comprising photobleaching nonactivated and unreacted portions of said photosensitive agent to controllably stop the biological effect thereof.

18. The method of claim 1 where said biological tissue has a histological state and where reacting said activated photosensitive agent with said biological tissue to obtain said predetermined biological effect comprises changing said histological state of said biological tissue to include a thrombosis therein.

19. The method of claim 1 where said spatially selected biological tissue has a vascularity and where reacting said activated photosensitive agent with said spatially selected biological tissue to obtain said predetermined biological effect comprises removing said vascularity of spatially selected biological tissue and keeping fibrosis from occurring therein.

20. The method of claim 1 where said biological tissue has a vascularity and is a selected site in the eye, where delivering a photosensitive agent is spatially delivered to said selected site in the eye, where activating a spatially selected portion of said photosensitive agent with electromagnetic radiation is exposing only a spatially selected area of said selected site to electromagnetic radiation, and where reacting said activated photosensitive agent with said biological tissue to obtain said predetermined biological effect is reacting only said photosensitive agent in said spatially selected area of said selected site to remove said vascularity of said biological tissue therein and to keep fibrosis from occurring therein.

* * * * *

UNITED STATES PATENT AND TRADEMARK OFFICE
CERTIFICATE OF CORRECTION

PATENT NO. : 6,095,147  
DATED : August 1, 2000  
INVENTOR(S) : Hill et al.

Page 1 of 1

It is certified that error appears in the above-identified patent and that said Letters Patent is hereby corrected as shown below:

<u>Title page,</u>  
Assignees, -- The Regents of the University of California, Oakland, California and Miravant Systems, Inc., formerly PDT Systems, Inc., Santa Barbara, California --.

Signed and Sealed this

Sixteenth Day of April, 2002

*Attest:*

JAMES E. ROGAN  
*Attesting Officer*     *Director of the United States Patent and Trademark Office*